(12) United States Patent
Juan

(10) Patent No.: US 7,684,845 B2
(45) Date of Patent: *Mar. 23, 2010

(54) PHYSIOLOGICAL MEASUREMENT DISPLAY

(75) Inventor: Cheng-Pin Juan, Taichung (TW)

(73) Assignee: G Pulse International Co., Ltd., Taichung (TW)

(*) Notice: Subject to any disclaimer, the term of this patent is extended or adjusted under 35 U.S.C. 154(b) by 560 days.

This patent is subject to a terminal disclaimer.

(21) Appl. No.: 11/590,485

(22) Filed: Nov. 1, 2006

(65) Prior Publication Data

US 2008/0139892 A1 Jun. 12, 2008

(51) Int. Cl.
A61B 5/04 (2006.01)
A61B 5/00 (2006.01)
A61B 5/05 (2006.01)

(52) U.S. Cl. .................. 600/390; 600/300; 600/386; 600/503; 600/547

(58) Field of Classification Search ................ 600/300, 600/386, 390, 503, 547, 595
See application file for complete search history.

(56) References Cited

U.S. PATENT DOCUMENTS

| | | | | |
|---|---|---|---|---|
| 3,851,320 A * | 11/1974 | Dahl | ............ | 340/870.17 |
| 3,863,626 A * | 2/1975 | Huber | ............ | 600/519 |
| 3,978,849 A * | 9/1976 | Geneen | ............ | 600/503 |
| 4,129,125 A * | 12/1978 | Lester et al. | ............ | 600/484 |
| 4,516,581 A * | 5/1985 | Sessions | ............ | 600/396 |
| 4,638,807 A * | 1/1987 | Ryder | ............ | 600/383 |
| 4,709,704 A * | 12/1987 | Lukasiewicz | ............ | 600/382 |
| 4,889,131 A * | 12/1989 | Salem et al. | ............ | 600/484 |
| 4,909,260 A * | 3/1990 | Salem et al. | ............ | 600/534 |
| 4,966,154 A * | 10/1990 | Cooper et al. | ............ | 600/484 |
| 5,353,793 A * | 10/1994 | Bornn | ............ | 600/386 |
| 5,491,474 A * | 2/1996 | Suni et al. | ............ | 340/870.31 |
| 5,778,880 A * | 7/1998 | Chen | ............ | 600/509 |
| 6,093,158 A * | 7/2000 | Morris | ............ | 600/590 |
| 6,272,365 B1 * | 8/2001 | Ronkainen et al. | ............ | 600/390 |
| 6,530,886 B1 * | 3/2003 | Ishida et al. | ............ | 600/442 |
| 6,760,610 B2 * | 7/2004 | Tschupp et al. | ............ | 600/345 |
| 7,330,751 B2 * | 2/2008 | Ueda | ............ | 600/509 |
| 7,428,433 B2 * | 9/2008 | Juan | ............ | 600/390 |
| 2005/0096556 A1 * | 5/2005 | Hsieh Chen | ............ | 600/509 |
| 2006/0058695 A1 * | 3/2006 | Chen | ............ | 600/509 |

* cited by examiner

*Primary Examiner*—Max Hindenburg
*Assistant Examiner*—Sean P Dougherty

(57) ABSTRACT

A physiological measurement display comprises: a strip having: at least one conductive portion at an inner side thereof; an electronic device connected to the conductive portion; the electronic device having at least one physiological measure unit; and a display panel at an outer side of the electronic device for displaying physiological data from the physiological measure unit. The electronic device is installed with a level meter, or alarm lights or a speaker. The display panel is pivotally installed to the electronic device and is turnable for viewing. Two ends of the electronic device have buckling grooves and two ends of the strip have buckles engageable to the buckling grooves. The buckles and buckling grooves are conductive. The electronic device is installed with an auxiliary conductive portion or a conductive rubber.

7 Claims, 10 Drawing Sheets

PHYSIOLOGICAL MEASUREMENT DISPLAY

FIELD OF THE INVENTION

The present invention relates to a physiological measurement display, wherein physiological measurement display provides the function of display, alarm light, speaker and level meter so as to provide various information to users. Furthermore, the display is turnable so that the user can view the data at different views.

BACKGROUND OF THE INVENTION

The prior art physiological measurement strip has an elastic strip and a measure unit. The measure unit has a main body and a signal processor. The main body is made of flexible material and a backside thereof has two conductive cloths. The signal processor is installed at a front side of the main body and is electrically conductive to the conductive cloth. Two ends of the elastic strip are buckled to the main body for being worn on the breast of the user. The conductive cloths of the measure unit are adhered to the skin of the user so as to measure physiological data. The data is transferred to a computer, a PDA, a handset, etc. wirelessly so that the user and medical persons can assure the state of the users.

However, the prior art physiological measurement strip can measure physiological information to prevent accidents. As a whole, it is not an ideal one, this is because the physiological measurement display has only one LCD display light to indicate whether it is operated normally, but no display is installed to show the data real time. Thus various forms of receivers are used. However this is inconvenient.

Furthermore in emergency, the physiological measurement unit of the prior art has no auxiliary function to alert the user or medical persons. Furthermore, the design of the prior art can not be matched to persons of different sizes. For those persons with great sizes, they are not suitable for wearing the physiological measurement unit and thus the measurement data are not accuracy.

SUMMARY OF THE INVENTION

Accordingly, the primary object of the present invention is to provide a physiological measurement display, wherein physiological measurement display provides the function of display, alarm light, speaker and level meter so as to provide various information to users. Furthermore, the display is turnable so that the user can view the data at different views.

To achieve above objects, the present invention provides a physiological measurement display which comprises a strip having: at least one conductive portion at an inner side thereof; an electronic device connected to the one conductive portion; the electronic device having at least one physiological measure unit; and a display panel at an outer side of the electronic device for displaying physiological data from the physiological measure unit. The electronic device is installed with a level meter, or alarm lights or a speaker. The display panel is pivotally installed to the electronic device and is turnable for viewing. Two ends of the electronic device have buckling grooves and two ends of the strip have buckles engageable to the buckling grooves; the buckles and buckling grooves are conductive. The electronic device is installed with an auxiliary conductive portion or a conductive rubber.

The various objects and advantages of the present invention will be more readily understood from the following detailed description when read in conjunction with the appended drawing.

DETAILED DESCRIPTION OF THE INVENTION

Figure 1:
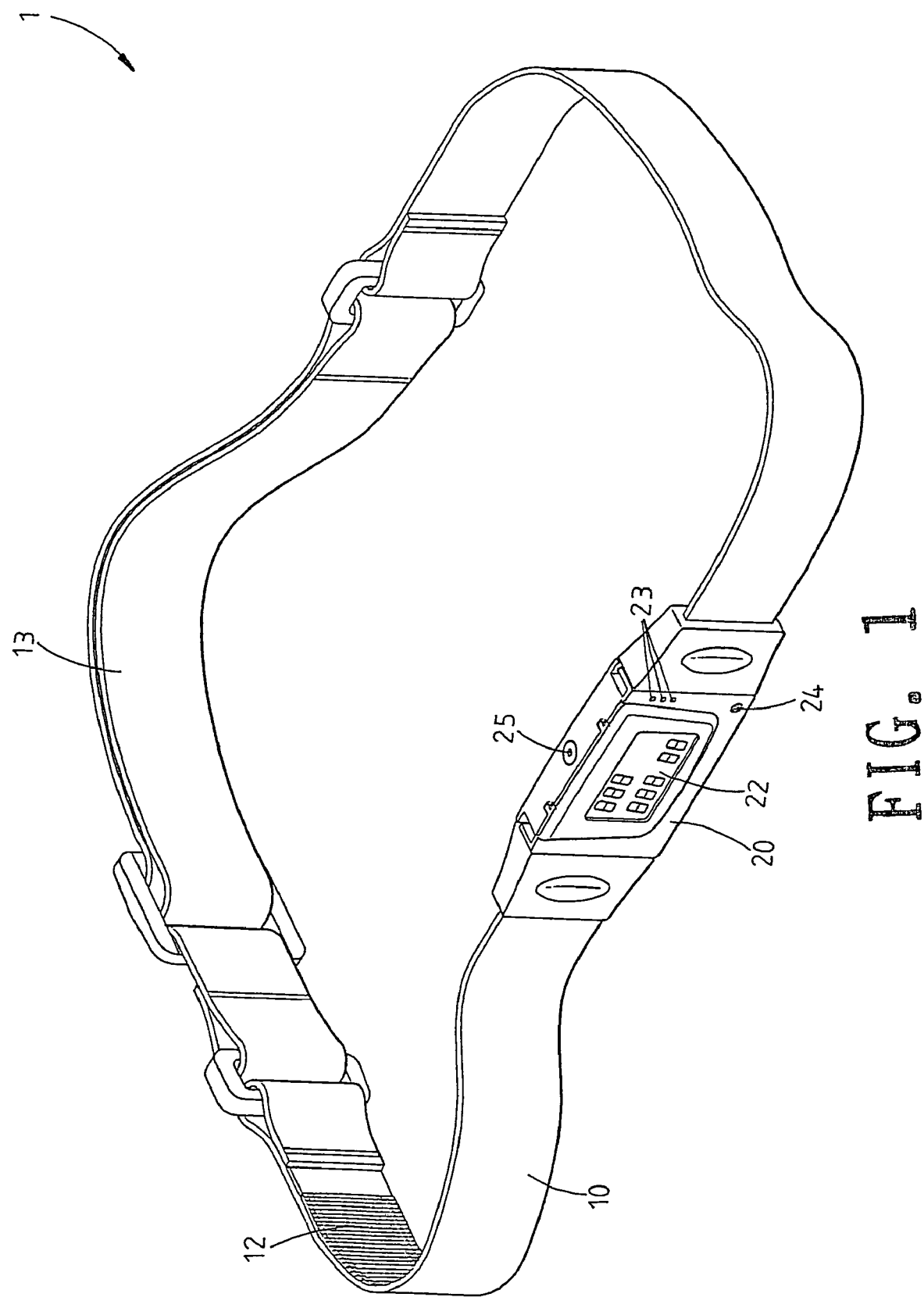
FIG. 1 is a perspective view of the physiological measurement display of the present invention.

In order that those skilled in the art can further understand the present invention, a description will be provided in the following in details. However, these descriptions and the appended drawings are only used to cause those skilled in the art to understand the objects, features, and characteristics of the present invention, but not to be used to confine the scope and spirit of the present invention defined in the appended claims.

Referring to FIGS. 1 to 4, the physiological measurement display 1 of the present invention is illustrated. The present invention has the following elements.

A strip 10 has two ends which are formed as buckles 11. Each buckle 11 is conductive. An interior of the strip 10 is installed with two conductive portions 12 made of conductive material. The conductive portions 12 may have a form of a web, a stripe, or a sheet. The conductive portions 12 are in contact with the body of the user for the purpose of measurement. The strip 10 is installed with an adjustment section 13 for adjusting a length of the strip 10.

An electronic device 20 is connected to the strip 10. The electronic device 20 has two ends which are formed as buckling grooves 21 for receiving the buckles 11 of the strip 10. An interior of the buckling grooves 21 are conductive so that the electronic device 20 is electrically connected to the strip 10 through the buckling grooves 21. The electronic device 20 is installed with a processor therein (not shown) so as to measure the physiological data of the user. An outer side of the electronic device 20 is pivotally installed to one end of a display panel 22. The display panel 22 serves to display the measuring data of the electronic device 20. The display panel 22 is turnable for viewing. The electronic device 20 is installed with alarm lights 23 of various colors and a speaker 24 for indication. The alarm lights 23 include a red light, a green light and a yellow light for showing different levels of alert conditions. The electronic device 20 is installed with a level meter 25 which has buoyant ball for viewing the horizontality and orientation of the users who are not good in equilibrium.

Figure 2:
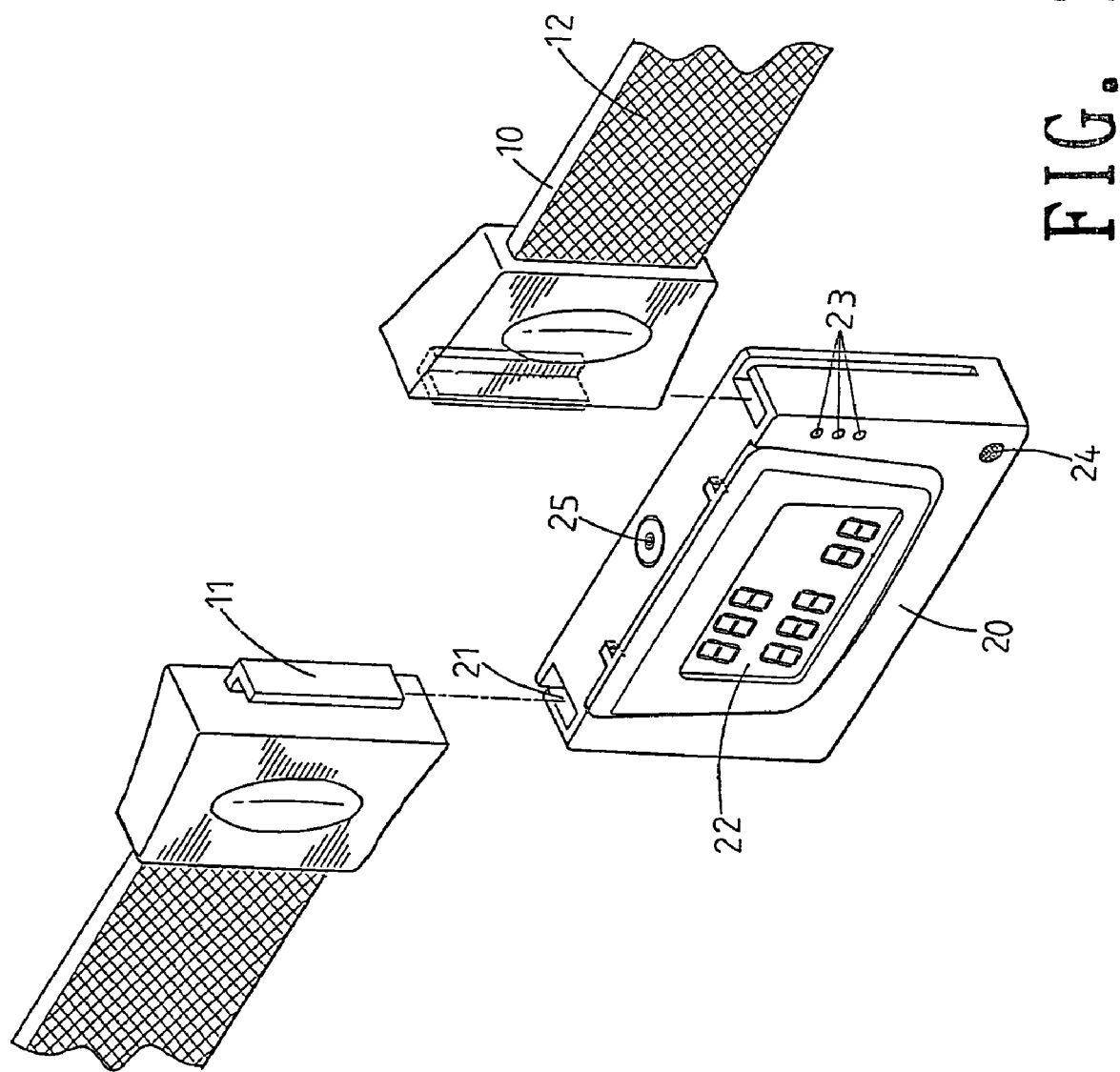
FIG. 2 is a partial exploded perspective view of the physiological measurement display of the present invention.

In use of the present invention, the adjustment section 13 is used to adjust the length of the strip 10, as illustrated in FIG. 2. The buckles 22 are buckled with the buckling grooves 21 of the electronic device 20. Then the conductive portions 12 of the strip 10 are conductive to the electronic device 20. The conductive portion 12 is adhered to the surface of the body of the user. Thus the measurement units in the electronic device 20 can measure the physiological data of the user, such as pulse rates, body temperature, etc. Other than wireless transmission functions, the electronic device 20 can provide physiological data through the display panel 22, alarm lights 23, speaker 24 and level meter 25.

Figure 3:
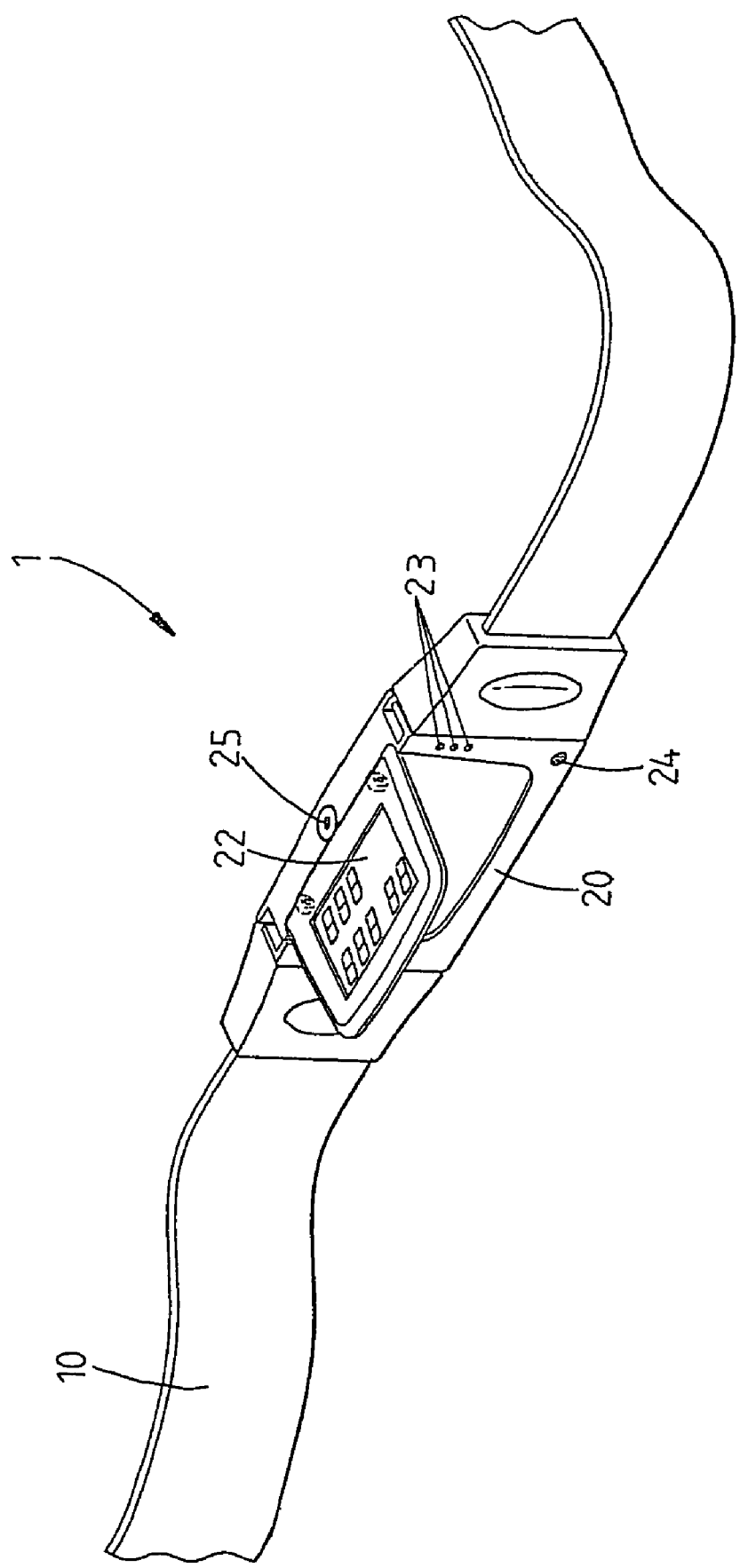
FIG. 3 is a schematic view showing the rotating operation of the physiological measurement display of the present invention.
Figure 4:
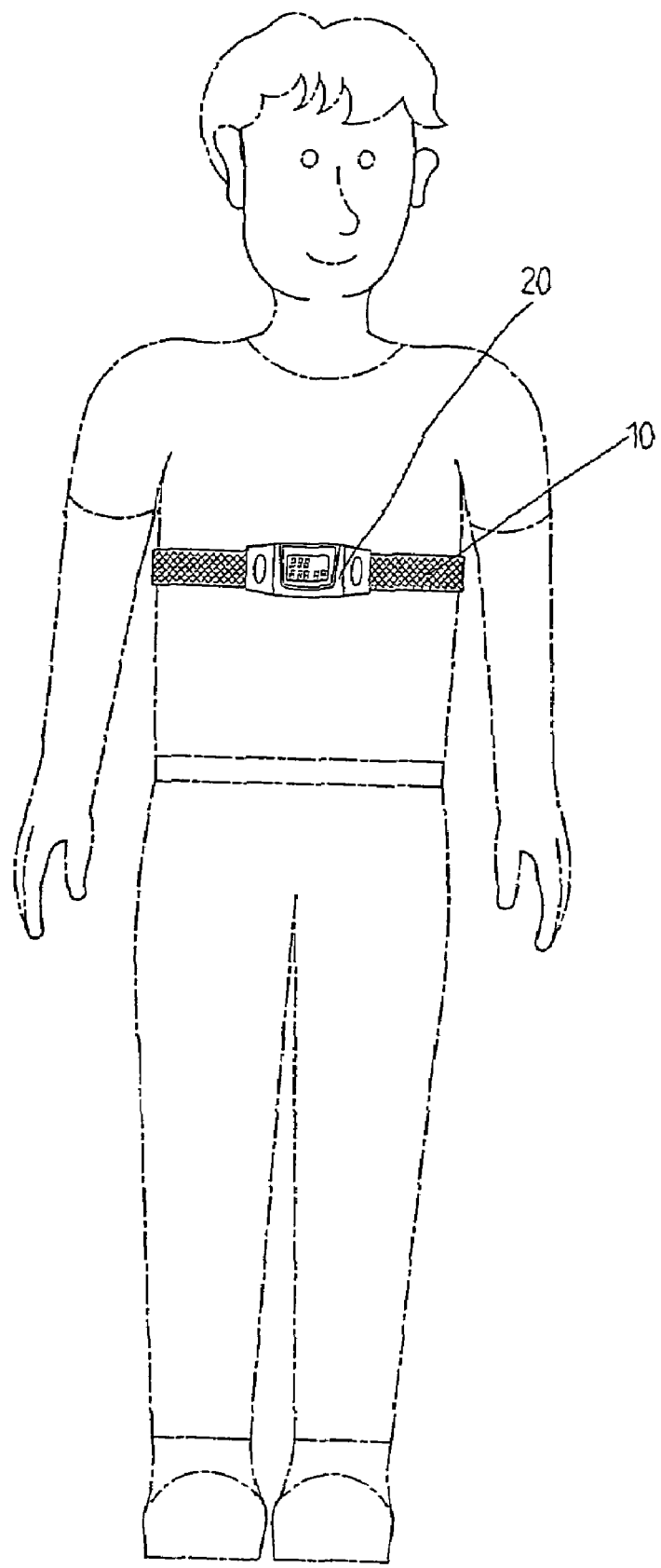
FIG. 4 is a schematic view showing the use of the display unit of the physiological measurement display of the present invention.

Referring to FIG. 3, when the display panel 22 rotates upwards to a predetermined angle, the user can view the data on the display panel 22.

Moreover, the electronic device 20 is installed with auxiliary indications, such as alarm lights 23, and the speaker 24. The alarm lights 23 have different alert levels through the color of the lights. For example green light displays that the physiological data is normal, yellow light displays that the physiological data is not good, and red light displays that the physiological data is in an emergency state.

The level meter 25 serves to help the user of bad equilibrium. The level meter 25 has a sealing space which is filled with liquid. The sealing space has an indicator with a density smaller than that of the liquid. Thereby the user can understand the equilibrium of the user.

Figure 5:
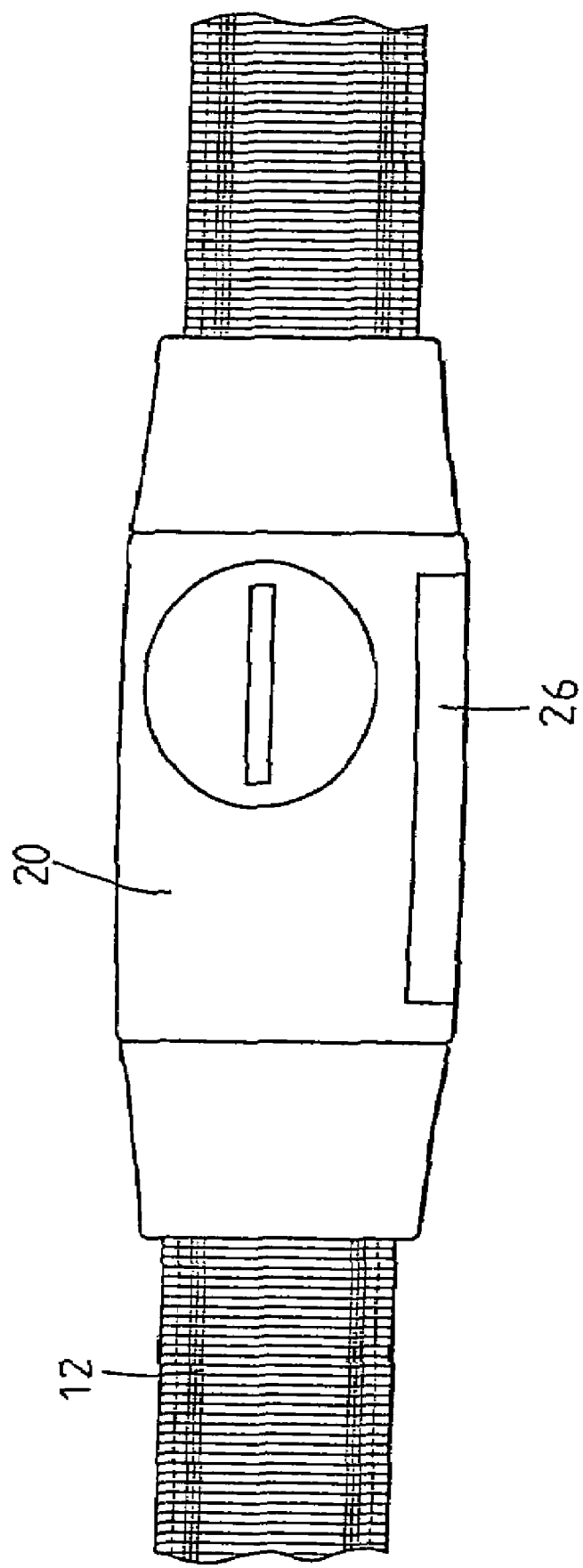
FIG. 5 is a rear plane view showing the auxiliary conductive portion of the present invention in the second embodiment of the present invention.
Figure 6:
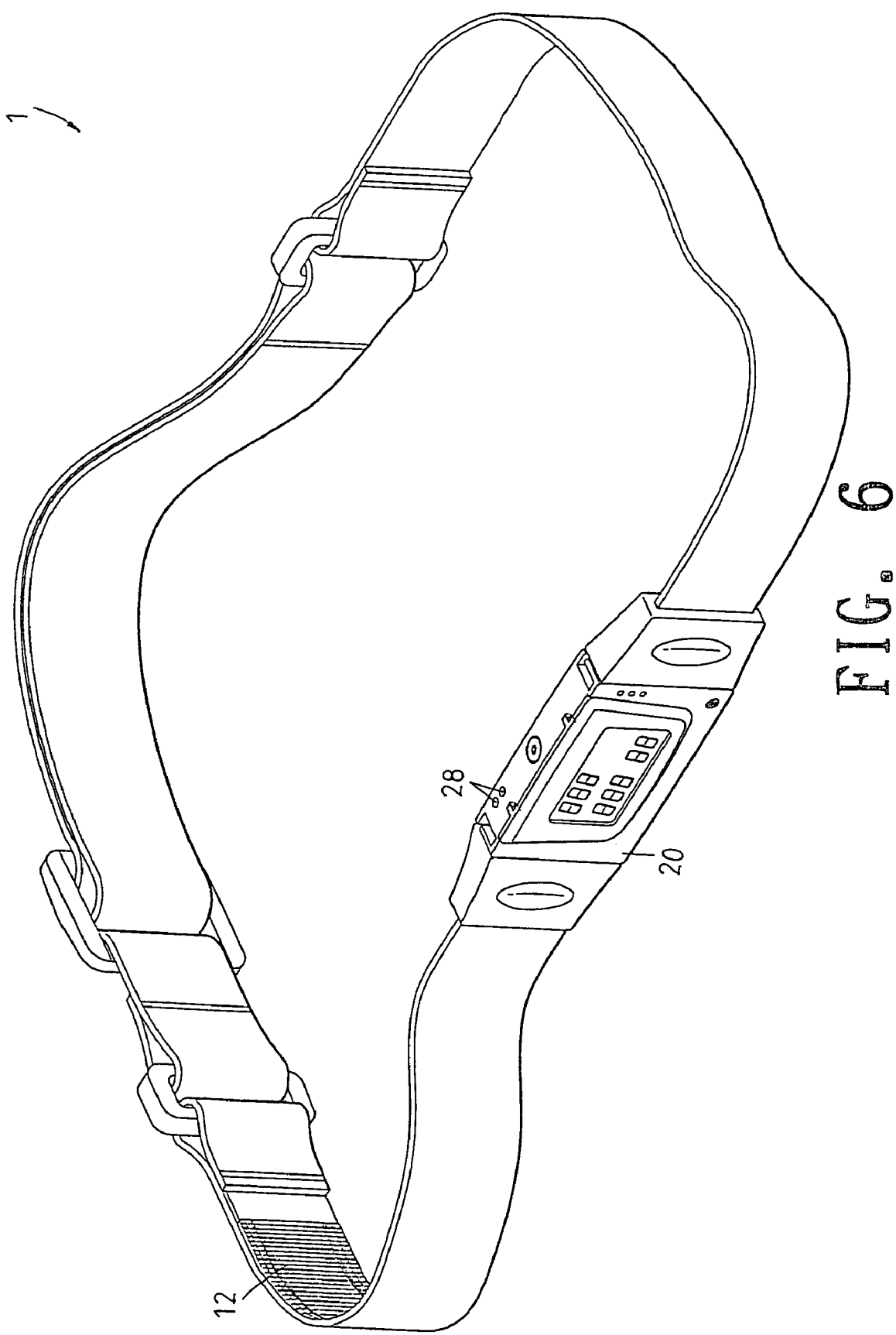
FIG. 6 is a perspective view of the third embodiment of the present invention.
Figure 7:
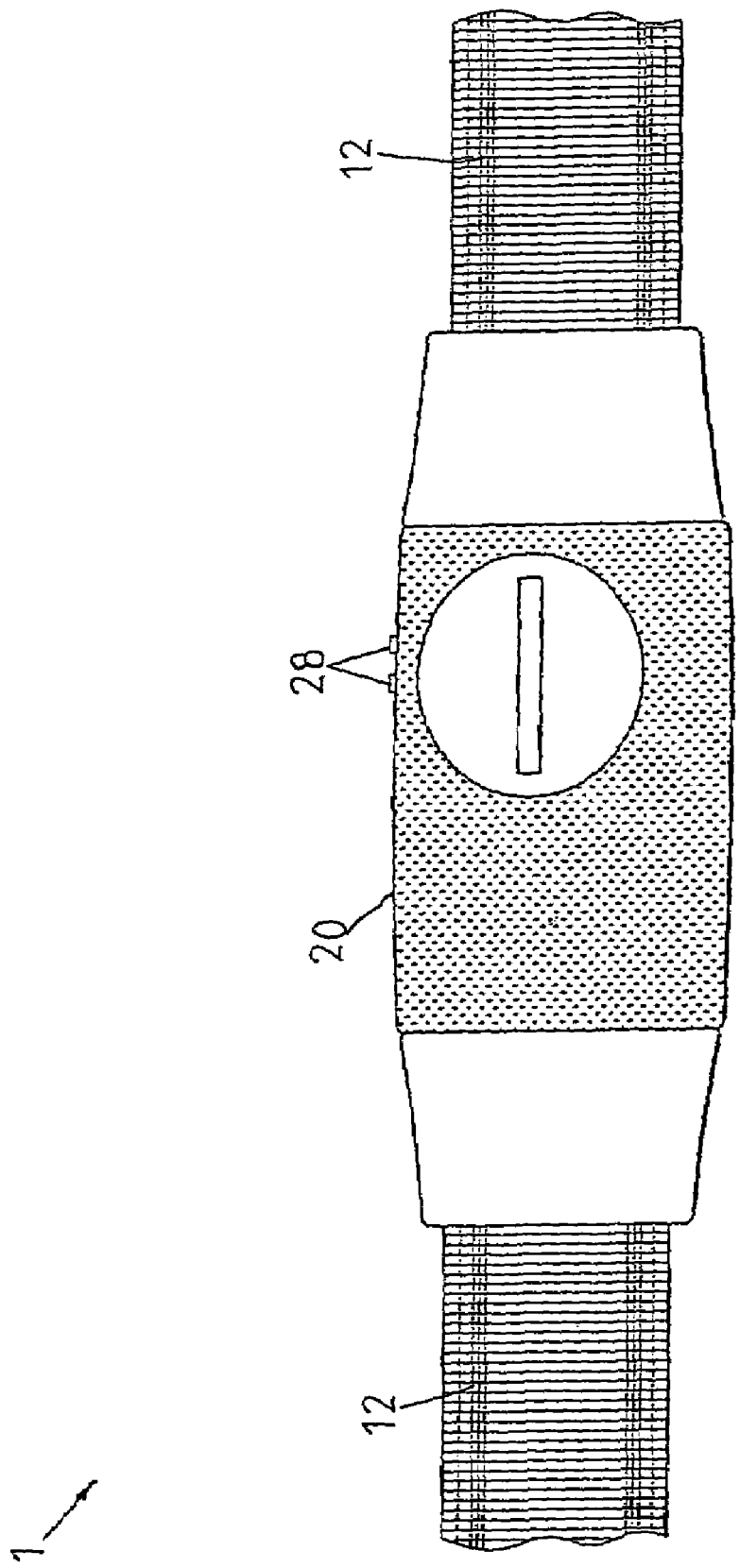
FIG. 7 is a rear plane view of the third embodiment of the present invention.

Referring to FIG. 5, the second embodiment of the physiological measurement display of the present invention is illustrated. In this embodiment, those identical to the above embodiment will not be further described herein. Only those different from above embodiment are described.

A backside of the electronic device 20 can be installed with an auxiliary conductive portion 26 which can perform the measurement in three points with the function of the conductive portion 12 so that the data has waveform and is more accurate.

Referring to FIGS. 6 to 10, the third embodiment of the present invention is illustrated. In this embodiment, those identical to the above embodiment will not be further described herein. Only those different from above embodiment are described.

A backside of the electronic device 20 is adhered with a conductive rubber 27 and an upper end of the electronic device 20 is formed with two insertion holes 28.

Figure 8:
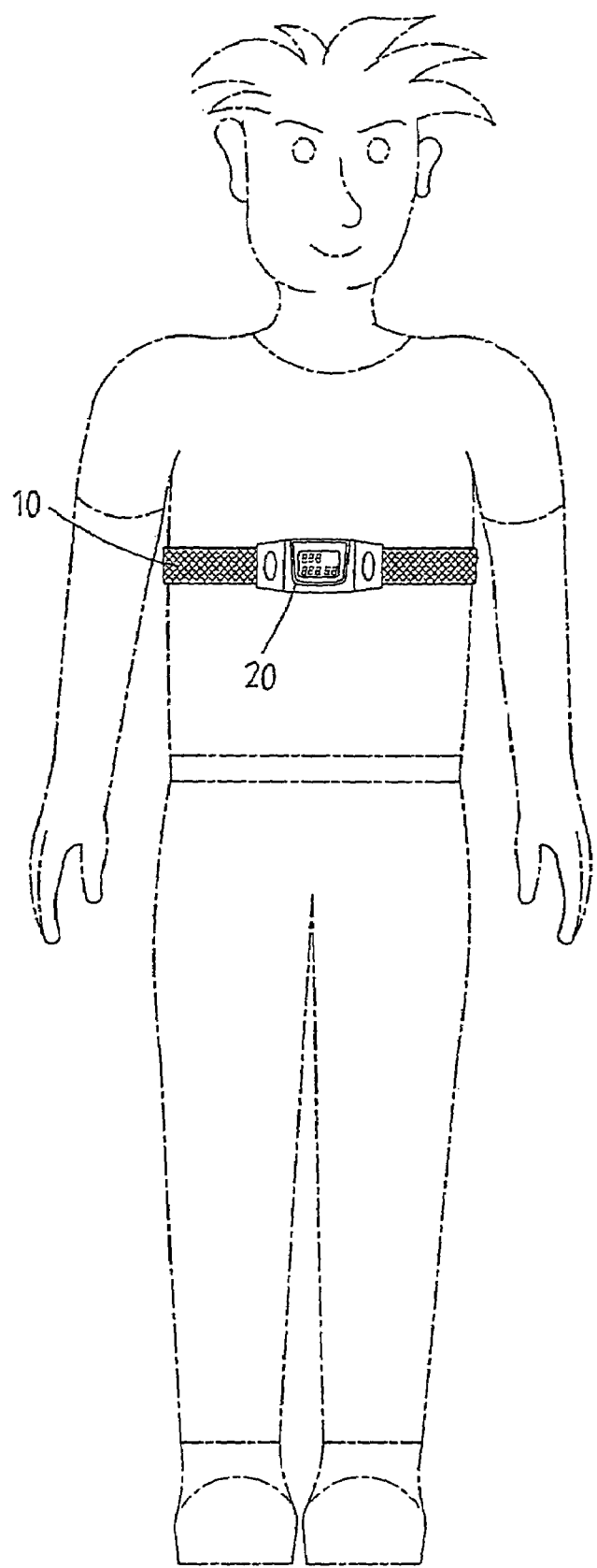
FIG. 8 is a schematic view showing the use of the third embodiment of the present invention.

Referring to FIG. 8, when using the present invention, the conductive rubber 27 and the conductive portions 12 are used to measure the body at three points so as to have information with waveform.

Figure 9:
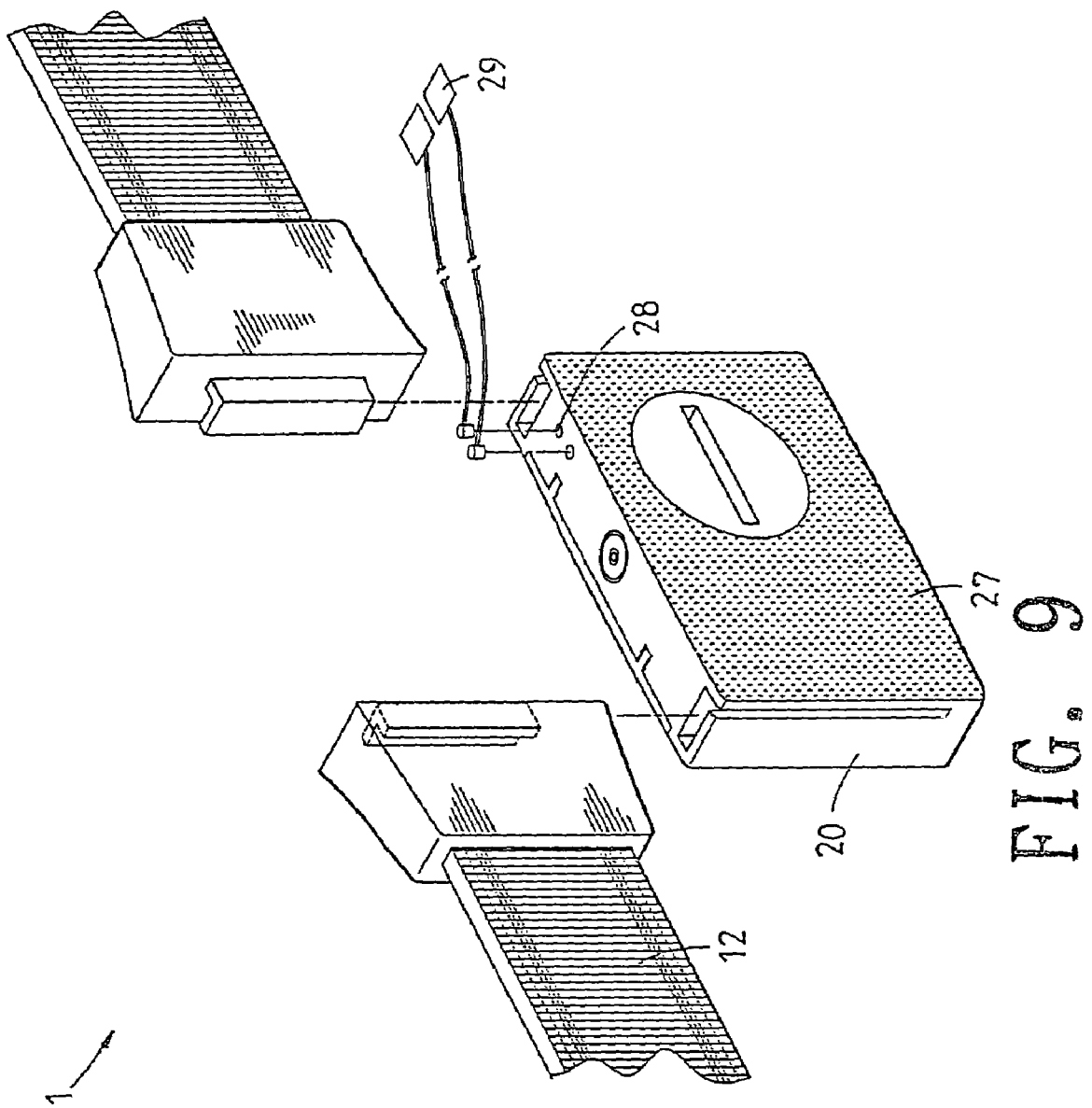
FIG. 9 is a partial exploded perspective view of the third embodiment of the present invention.
Figure 10:
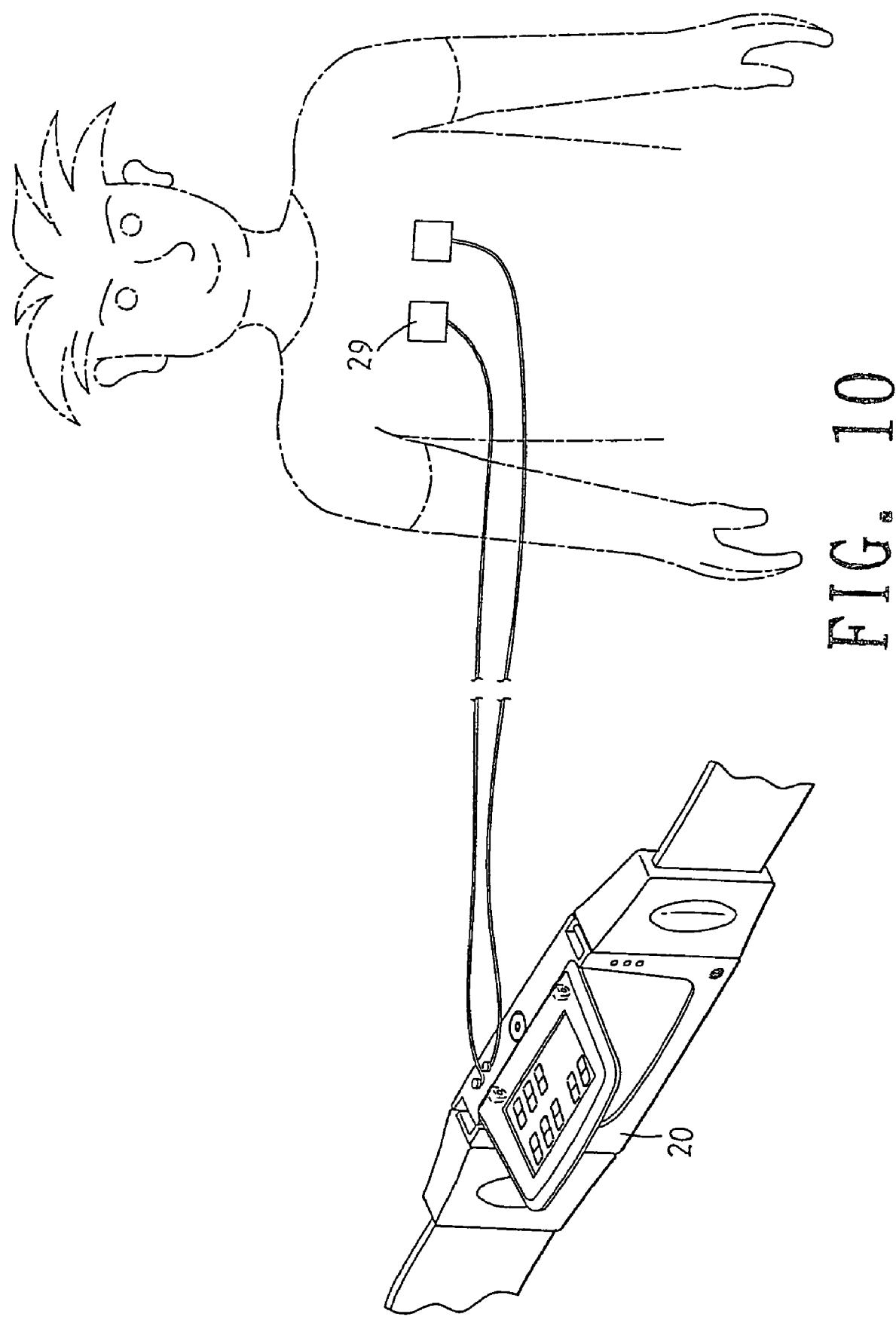
FIG. 10 is a schematic view showing the operation of the conductive plate in the third embodiment of the present invention.

Referring to FIGS. 9 and 10, each insertion hole 28 of the electronic device 20 can be connected to an external conductive plate 29. The two external conductive plates 29, the two conductive portions 12 and the conductive rubber 27 are provided to measure the body information at four different points. Or the conductive plate 29 can be independently adhered to the body of the user for measuring the physiological information of the user.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A physiological measurement display comprising:
a strip having at least one conductive portion at an inner side thereof; the strip having two buckles respectively disposed in two ends thereof; wherein each buckle is conductive; the strip having an adjustment section disposed therein for adjusting a length of the strip;
an electronic device connected to the one conductive portion; the electronic device having at least one physiological measure unit; the electronic device having two buckling grooves respectively formed in two ends thereof; wherein each groove is conductive and each buckle engages with each buckling groove; and
a display panel connected to an outer side of the electronic device for displaying physiological data from the physiological measure unit;
wherein the display panel is pivotally installed to the electronic device for viewing physiological data on the display panel.

2. The physiological measurement display as claimed in claim 1, wherein the electronic device is installed with a level meter.

3. The physiological measurement display as claimed in claim 1, wherein a backside of the electronic device is installed with an auxiliary conductive portion for increasing the accuracy of measurement.

4. The physiological measurement display as claimed in claim 1, wherein a backside of the electronic device is installed with conductive rubbers for increasing the accuracy of measurement.

5. The physiological measurement display as claimed in claim 1, wherein the electronic device has at least one insertion hole defined therein and at least one external conductive plate connected to the one insertion hole for increasing the accuracy of measurement.

6. The physiological measurement display as claimed in claim 1, wherein the electronic device is installed with alarm lights for displaying physiological conditions by various colors of the alarm lights.

7. The physiological measurement display as claimed in claim 1, wherein the electronic device is installed with a speaker.

* * * * *